(12) United States Patent
Alferness et al.

(10) Patent No.: US 6,230,714 B1
(45) Date of Patent: *May 15, 2001

(54) CARDIAC CONSTRAINT WITH PRIOR VENUS OCCLUSION METHODS

(75) Inventors: Clifton A. Alferness, Redmond, WA (US); Donald F. Palme, Princeton; James Edward Shapland, Vadnais Heights, both of MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/193,260

(22) Filed: Nov. 18, 1998

(51) Int. Cl.$^7$ .................................................. A61B 19/00
(52) U.S. Cl. ............................................. 128/898; 600/37
(58) Field of Search .................................. 623/11, 66, 1, 623/2; 128/898; 600/37, 17; 606/157

(56) References Cited

U.S. PATENT DOCUMENTS

| | | |
|---|---|---|
| 3,983,863 | 10/1976 | Janke et al. . |
| 4,048,990 | 9/1977 | Goetz . |
| 4,403,604 | 9/1983 | Wilkinson et al. . |

FOREIGN PATENT DOCUMENTS

| | | |
|---|---|---|
| 295 17 393 U1 | 3/1996 | (DE) . |
| 0 280 564 | 8/1988 | (EP) . |
| 60-203250 | 10/1985 | (JP) . |
| 1-145066 | 6/1989 | (JP) . |
| 1009457 | 4/1983 | (SU) . |
| WO 98/29041 | 7/1998 | (WO) . |
| WO 98/58598 | 12/1998 | (WO) . |

OTHER PUBLICATIONS

Oh et al., "The Effects of Prosthetic Cardiac Binding and Adynamic Cardiomyoplasty in a Model of Dilated Cardiomyopathy," *J. Thorac. Cardiovasc. Surg.*, 116:148–153 (1998).

Soccorso Capomolla et al., "Dobutamine and nitroprusside infusion in patients with severe congestive heart failure: Hemodynamic improvement by discordant effects on mitral regurgitation, left atrial function, and ventricular function," *American Heart Journal*, 134:1089–1098 (Dec. 1997).

Vaynblat et al., "Cardiac Binding in Experimental Heart Failure," *Ann. Thorac. Surg.*, 64:81–85 (1997).

C. Coletta et al., "Prognostic value of left ventricular volume response during dobutamine stress echocardiography," *Eur. Heart J.*, 18:1599–1605 (Oct. 1997).

Cohn, "The Management of Chronic Heart Failure", *The New Eng. J. of Med.*, 335 (7): 490–498 (Aug. 15, 1996).

Levin et al., "Reversal of Chronic Ventricular Dilation in Patients With End–Stage Cariomyopathy by Prolonged Mechanical Unloading", *Circulation* 91 (11): 2717–2720 (Jun. 1, 1995).

(List continued on next page.)

Primary Examiner—Corrine McDermott
Assistant Examiner—Kelley O'Hara
(74) Attorney, Agent, or Firm—Merchant & Gould P.C.

(57) ABSTRACT

A method for treating cardiac disease includes accessing a heart and restricting a blood supply to the heart to reduce a size of the heart. A constraining device is placed on the heart. The constraining device is secured to the heart with the constraining device having portions disposed on opposite sides of the heart to constrain circumferential expansion of the heart during diastole and permit unimpeded contraction of the heart during systole. Access to the heart is closed while leaving the constraining device in place on the heart.

8 Claims, 6 Drawing Sheets

U.S. PATENT DOCUMENTS

| | | |
|---|---|---|
| 4,428,375 | 1/1984 | Ellman . |
| 4,630,597 | 12/1986 | Kantrowitz et al. . |
| 4,690,134 | 9/1987 | Snyders . |
| 4,821,723 | 4/1989 | Baker, Jr. et al. . |
| 4,878,890 | 11/1989 | Bilweis . |
| 4,936,857 | 6/1990 | Kulik . |
| 4,957,477 | 9/1990 | Lundback . |
| 4,973,300 | 11/1990 | Wright . |
| 4,976,730 | 12/1990 | Kwan-Gett . |
| 5,057,117 | 10/1991 | Atweh . |
| 5,087,243 | 2/1992 | Avitall . |
| 5,131,905 | 7/1992 | Grooters . |
| 5,150,706 | 9/1992 | Cox et al. . |
| 5,186,711 | 2/1993 | Epstein . |
| 5,192,314 | 3/1993 | Daskalakis . |
| 5,256,132 | 10/1993 | Snyders . |
| 5,290,217 | 3/1994 | Campos . |
| 5,356,432 | 10/1994 | Rutkow et al. . |
| 5,383,840 | 1/1995 | Heilman et al. . |
| 5,385,156 | 1/1995 | Oliva . |
| 5,429,584 | 7/1995 | Chiu . |
| 5,507,779 | 4/1996 | Altman . |
| 5,524,633 | 6/1996 | Heaven et al. . |
| 5,603,337 | 2/1997 | Jarvik . |
| 5,647,380 | 7/1997 | Campbell et al. . |
| 5,702,343 | 12/1997 | Alferness . |
| 5,713,954 | 2/1998 | Rosenberg et al. . |
| 5,800,528 | 9/1998 | Lederman et al. . |

OTHER PUBLICATIONS

Kass et al., "Reverse Remodeling From Cardiomyoplasty in Human Heart Failure, External Constraint Versus Active Assist", *Circulation* 91 (9): 2314–2318 (May 1, 1995).

Abstract: Mikhail Vaynblat et al., "Cardiac Binding in Experimental Heart Failure," Abstract in Supplement to *Circulation* 92(8):1810 (Oct. 15, 1995).

Capouya, et al., "Girdling Effect of Nonstimulated Cariomayoplasty on Left Ventricular Function," *The Society of Thoracic Surgeons*, 56:867–871 (1993).

Revista Española de Cardiologia, vol. 51, No. 7, Jul. 1998 (Abstract in English).

CARDIAC CONSTRAINT WITH PRIOR VENUS OCCLUSION METHODS

BACKGROUND OF THE INVENTION

1. Field of the Invention

The present invention pertains to a method for treating heart disease. More particularly, the present invention is directed to a method for treating congestive heart disease and related valvular dysfunction.

2. Description of the Prior Art

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the commonly prescribed treatment. Drug therapy treats the symptoms of the disease and may slow the progression of the disease. Importantly, there is no cure for congestive heart disease. Even with drug therapy, the disease will progress. Further, he drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Congestive heart failure has an enormous societal impact In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In his procedure, the latissimus dorsi muscle (taken from the patients shoulder) is wrapped around the heart and chronically paced synchronously with ventricular systole. Pacing of the muscle results in muscle contraction to assist the contraction of the heart during systole.

Even though cardiomyoplasty has demonstrated symptomatic improvement, studies suggest the procedure only minimally improves cardiac performance. The procedure is highly invasive requiring harvesting a patient's muscle and an open chest approach (i.e., stemotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping, reducing its constraining benefits and is generally not susceptible to post-operative adjustment. Finally, the muscle may fibrose and adhere to the heart causing undesirable constraint on the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist,* 91 *Circulation* 2314–2318 (1995). Similarly, cardiac binding is described in Oh et al., *The Effects of Prosthetic Cardiac Binding and Adynamic Cardiomyoplasty in a Model of Dilated Cardiomyopathy,* 116 *J. Thorac. Cardiovasc. Surg.* 148–153 (1998), Vaynblat et al., *Cardiac Binding in*

*Experimental Heart Failure*, 64 Ann. Thorac. Surg. 81–85 (1997) and Capouya et al., *Girdling Effect of Nonstimulated Cardiomyoplasty on Left Ventricular Function*, 56 Ann. Thorac. Surg. 867–871 (1993).

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle into the aorta. Such surgeries are expensive. The devices are at risk of mechanical failure and frequently require external power supplies. TAH devices are used as temporary measures while a patient awaits a donor heart for transplant.

Commonly assigned U.S. Pat. No. 5,702,343 to Alferness dated Dec. 30, 1997 teaches a jacket to constrain cardiac expansion during diastole. Also, PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart.

A cardiac constraint device can be placed on an enlarged heart and fitted snug during diastole. Commonly assigned and co-pending U.S. patent application Ser. No. 09/114,757 filed Jul. 13, 1998 describes a method for pre-shrinking a heart prior to fitting a cardiac constraint jacket. This method includes a drug therapy to pre-shrink the heart. The present invention is directed to a method for placement of a cardiac constraint device with enhanced techniques for pre-shrinking the heart. A further object of the present invention is directed to such a method permitting greater control of the degree of pre-shrinkage of the heart.

SUMMARY OF THE INVENTION

According to a preferred embodiment of the present invention, a method is disclosed for treating congestive heart disease and related cardiac complications such as valvular disorders. The method includes accessing a heart and restricting a blood supply to the heart to reduce a size of the heart. A constraining device is placed on the heart. The constraining device is secured to the heart with the constraining device having portions disposed on opposite sides of the heart to constrain circumferential expansion of the heart during diastole and permit unimpeded contraction of said heart during systole. The site of access to the heart is closed while leaving said constraining device in place on said heart. The blood flow restriction is relieved after the constraining device is secured to the heart.

BRIEF DESCRIPTION OF THE DRAWINGS

FIG. 4A is a side elevation view of a diseased heart in diastole with the device of FIG. 4 in place;

DESCRIPTION OF THE PREFERRED EMBODIMENT

A. Congestive Heart Failure

Figure 1A:
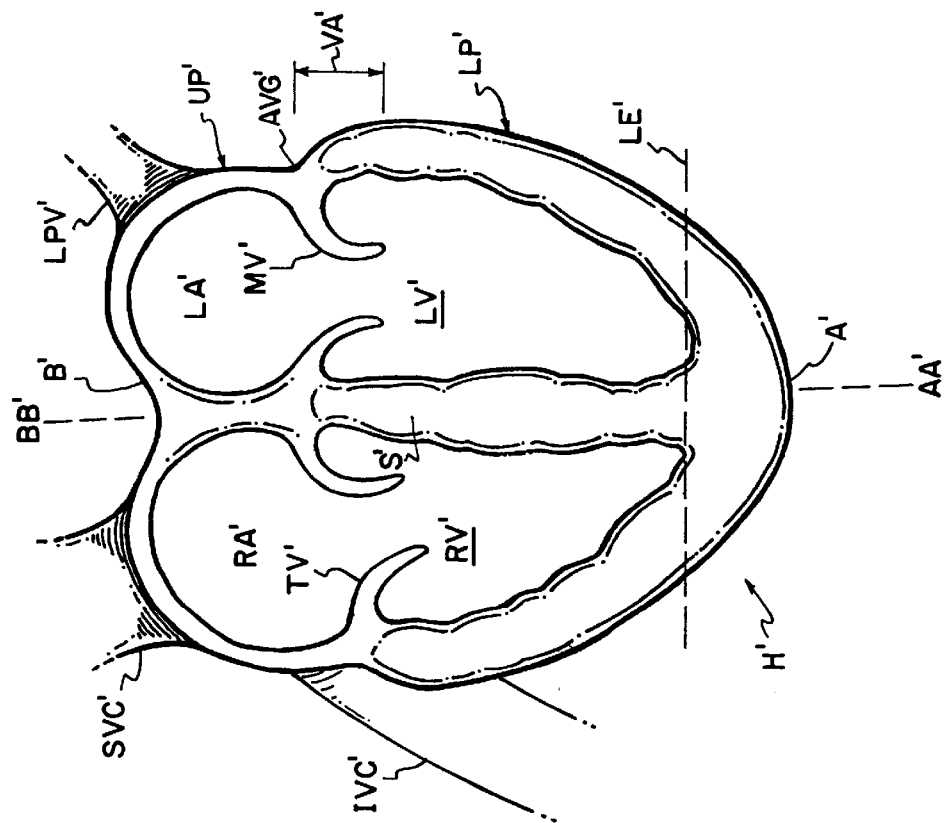
FIG. 1A is the view of FIG. 1 showing the heart during diastole.

To facilitate a better understanding of the present invention, description will first be made of a cardiac constraint device such as is more fully described in commonly assigned and copending U.S. patent application Ser. No. 09/114,757 now U.S. Pat. No 6,085,754 filed Jul. 13, 1998. In the drawings, similar elements are labeled similarly throughout.

Figure 1:
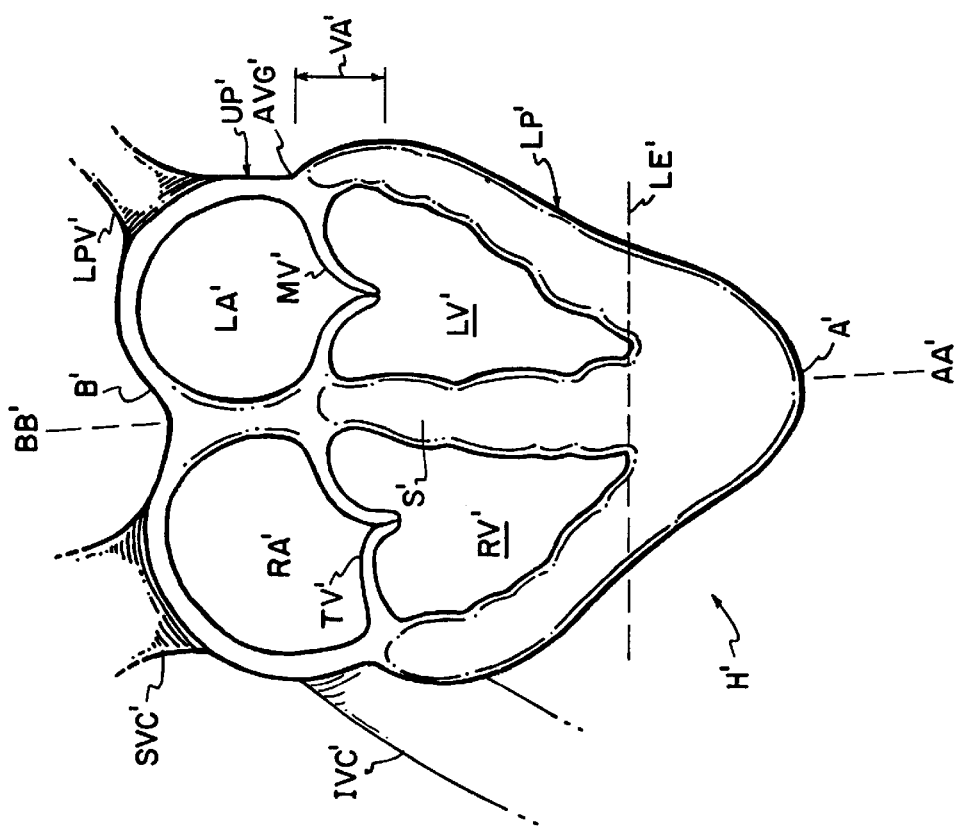
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis BB'-AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2A:
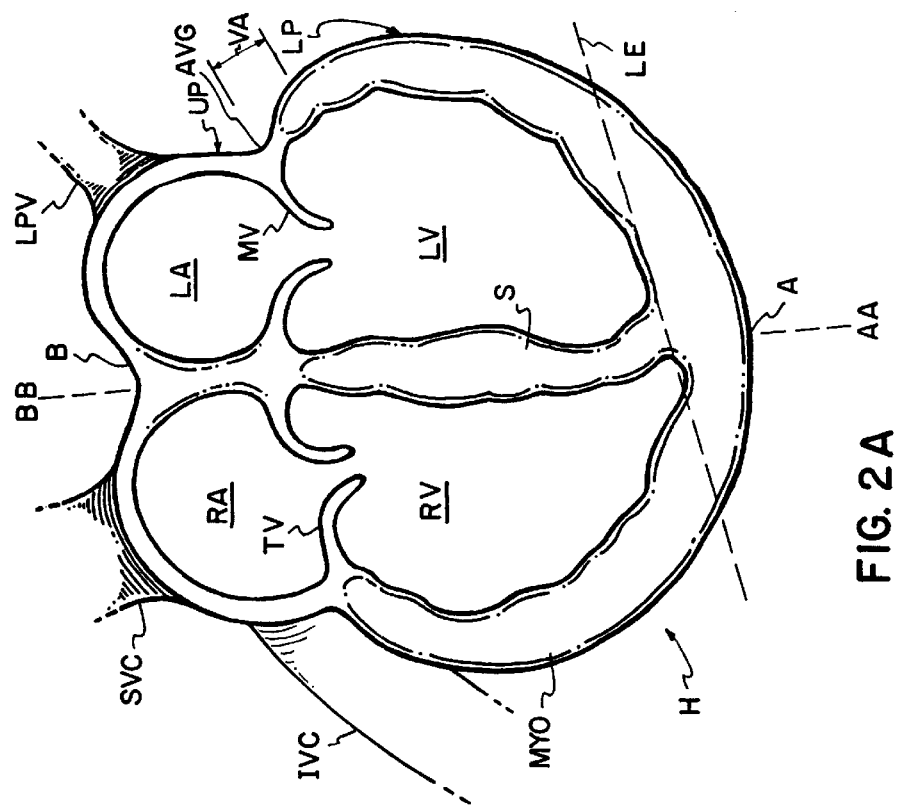
FIG. 2A is the view of FIG. 2 showing the heart during diastole.
Figure 2:
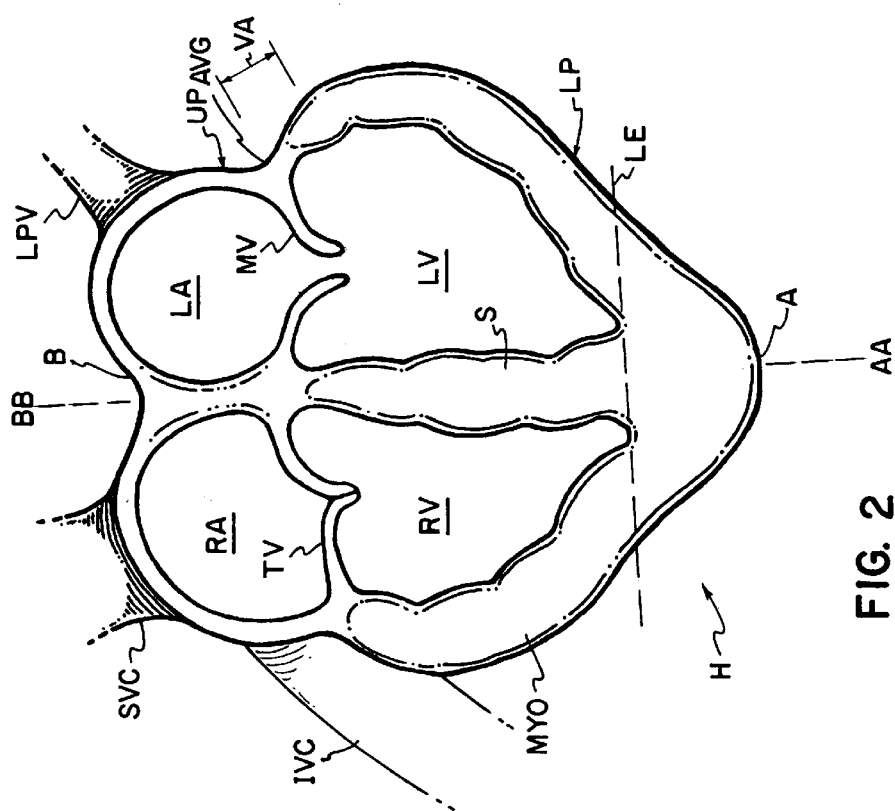
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Constraint Therapy

Having described the characteristics and problems of congestive heart disease, a treatment method and apparatus are described in commonly assigned and copending U.S. patent application Ser. No. 09/114,757 filed Jul. 13, 1998 now U.S. Pat. No. 6,085,754. In general, a jacket is configured to surround the myocardium MYO. While the method of the present invention will be described with reference to a jacket as described in commonly assigned and copending U.S. patent application Ser. No. 09/114,757 filed Jul. 13, 1998, it will be appreciated the present invention is applicable to any cardiac constraint device including those shown in U.S. Pat. No. 5,800,528 and PCT International Publication No. WO 98/29401.

Figure 3A:
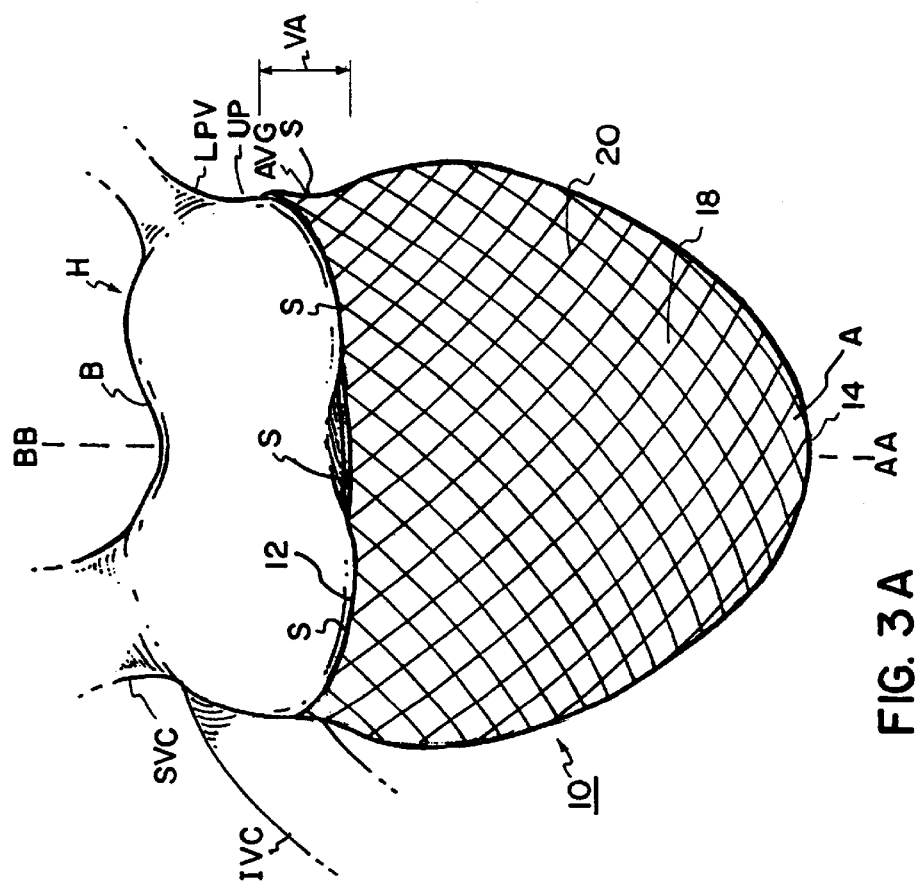
FIG. 3A is a side elevation view of a diseased heart in diastole with the device of FIG. 3 in place.
Figure 3:
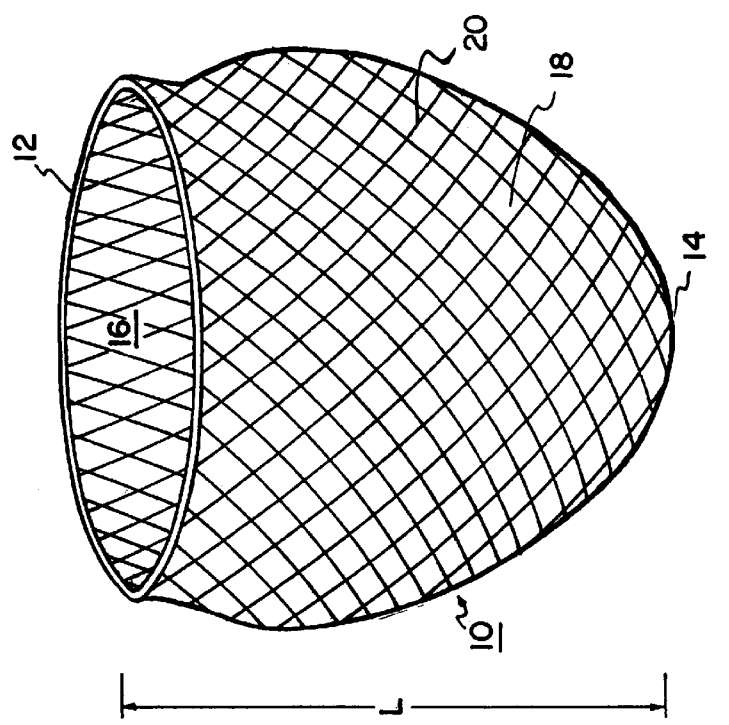
FIG. 3 is a perspective view of a cardiac constraint device to be used according to the method of the present invention.
Figure 4:
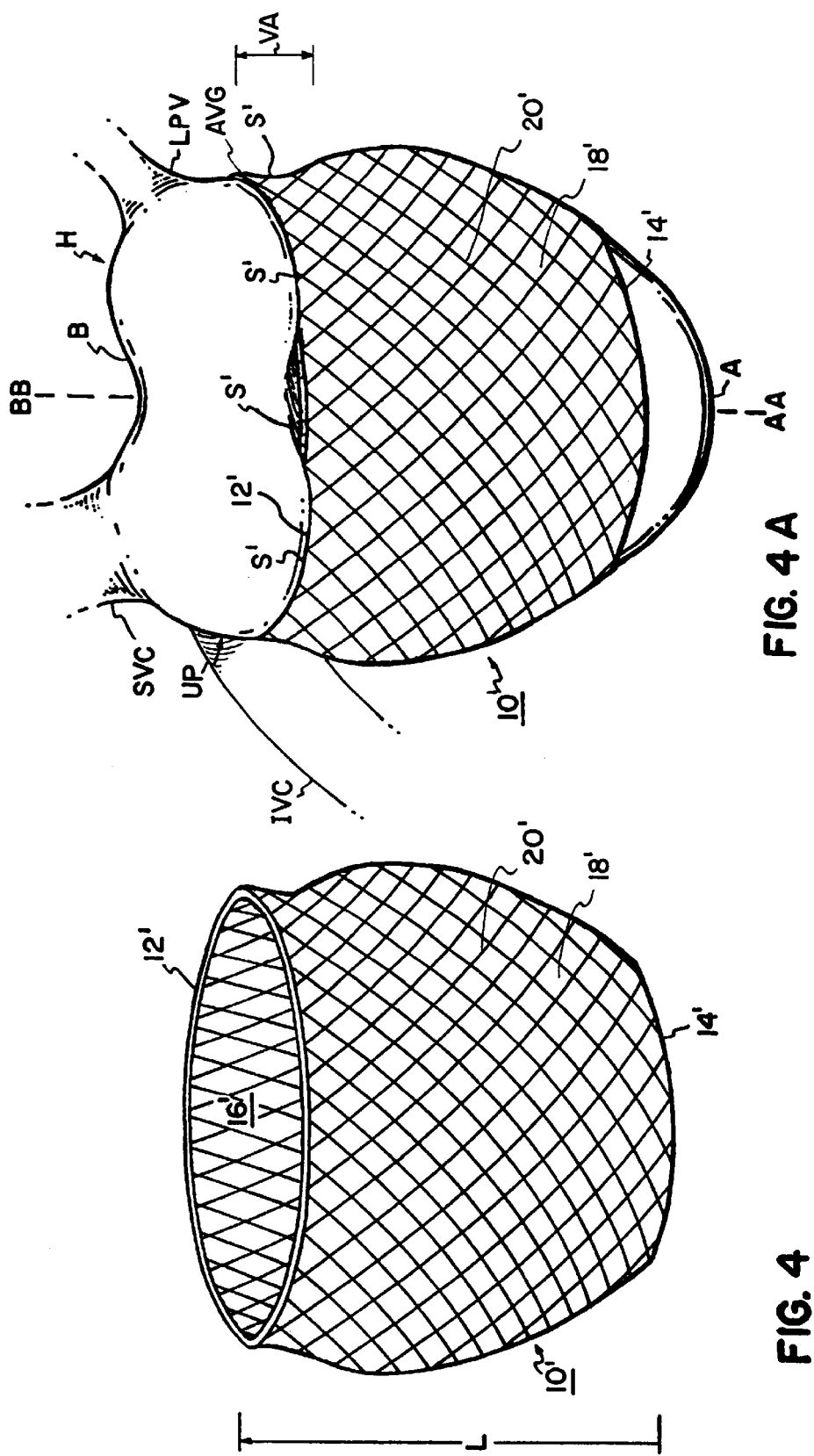
FIG. 4 is a perspective view of an alternative cardiac constraint device to be used according to the method of the present invention.

With reference now to FIGS. 3, 3A, 4 and 4A, the cardiac constraint device is shown as a jacket 10, 10' of flexible, biologically compatible material. The jacket 10, 10' is an enclosed knit material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures. The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

Figure 5:
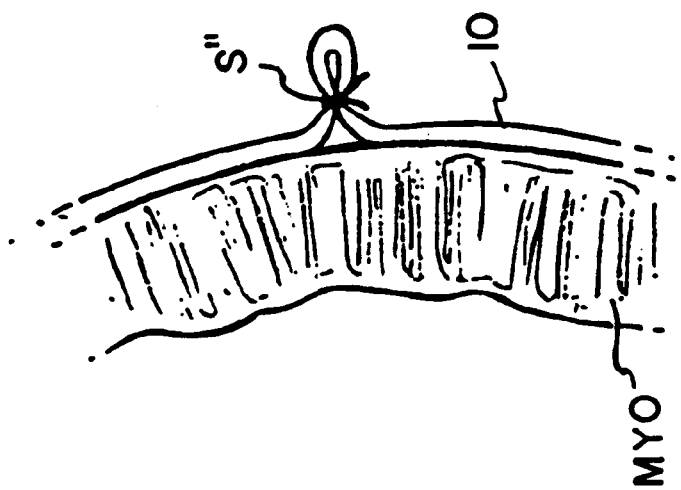
FIG. 5 is a cross-sectional view of the device of FIG. 3 overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other arrangements for adjusting volume. For example, as disclosed in U.S. Pat. No. 5,702,343, the jacket can be provided with a slot. The edges of the slot can be drawn together to reduce the volume of the jacket.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

While the jacket 10 is expandable due to its knit pattern, the fibers 20 of the knit fabric 18 are preferably non-expandable. While all materials expand to at least a small amount, the fibers 20 are preferably formed of a material with a low modulus of elasticity. In response to the low pressures in the heart H during diastole, the fibers 20 are non-elastic. In a preferred embodiment, the fibers are 70 Denier polyester. While polyester is presently preferred, other suitable materials include polytetrafluoroethylene (PTFE), expanded PTFE (ePTFE) and polypropylene.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

The fabric 18 is preferably tear and run resistant. In the event of a material defect or inadvertent tear, such a defect or tear is restricted from propagation by reason of the knit construction.

The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

C. Method of the Invention

As disclosed in commonly assigned and copending U.S. patent application Ser. No. 09/114,757 filed Jul. 13, 1998, heart size can be reduced at the time of placement in addition to preventing further enlargement. For example, the '757 application describes heart size reduction at the time of jacket placement through drugs (e.g., dobutamine, dopamine or epinephrine or any other positive inotropic agents) to reduce the heart size. The jacket is then snugly placed on the reduced size heart and prevents enlargement beyond the reduced size.

The present invention is directed to an improved alternative method for pre-shrinking the heart. Specifically, if blood flow to the heart is reduced, heart volume reduces. Even though the heart reduces, the heart maintains a natural shape dictated by its unique structure. This is a significant advantage over mechanical efforts to reduce heart size (such as external squeezing). Such efforts may succeed in reducing heart size but may do so while mis-shaping the heart.

Figure 6:
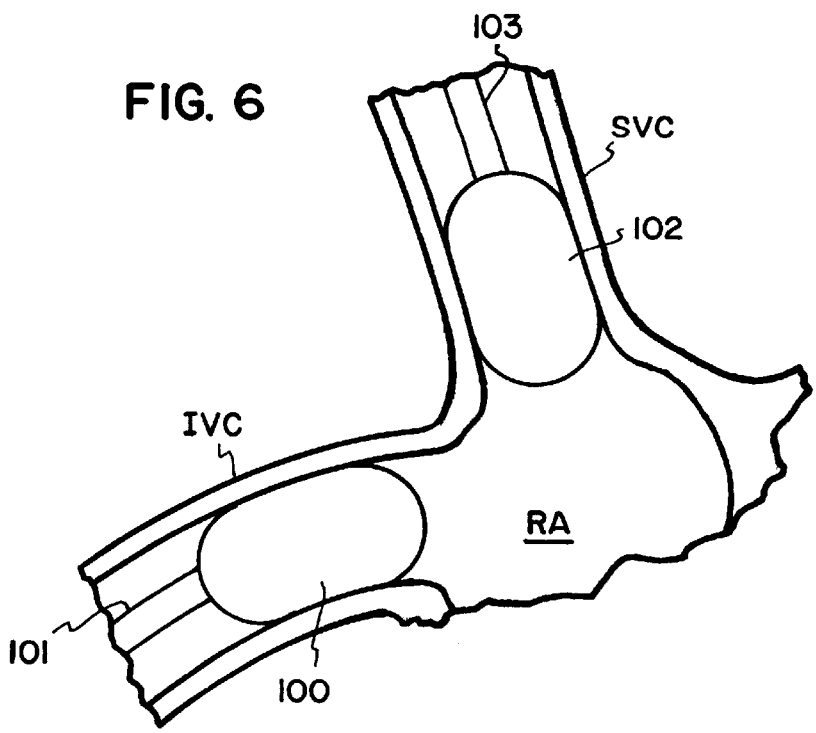
FIG. 6 is a view of the right atrium with inferior and superior vena cava occluded according to the method of the present invention.

With reference to FIG. 6, in one embodiment, heart size can be reduced by at least partially occluding veins supplying blood to the right atrium RA. Specifically, conventional balloon-tipped catheters 101, 103 are advanced to such veins and balloons 100, 102 are inflated. FIG. 6 shows balloons 100, 102 positioned within both the inferior and superior vena cava IVC, SVC. Inflation of one or both of the balloons 100, 102 reduces blood flow to the right atrium RA. After the left ventricle empties during systole, the presence of the balloons 100, 102 prevents the ventricle RV, LV from completely filling. As a consequence, heart volume shrinks while retaining normal heart shape. In FIG. 6 only the inferior and superior vena cava IVC, SVC are shown returning blood to the right atrium RA. Although not shown, other vessels also supply blood to the right atrium. If desired, these vessels can also be occluded to further reduce blood filling the heart and thus further reduce heart size.

In FIG. 6, balloons 100, 102 are shown to restrict blood flow through the inferior and superior vena cava IVC, SVC. Alternative restricting techniques could be used (e.g., clamping the veins from the exterior of the vein).

To place the jacket 10, 10' (or such other cardiac restraint device), the jacket 10, 10' may be placed over the heart H before the occlusion of the veins IVC, SVC. Subsequent to such occlusion and following the resultant heart size reduction, the jacket 10, 10' can then be snugly tightened on the heart H during diastole as previously described. Alternatively, the jacket 10, 10' can be placed on the heart H after occlusion and reduction and then snugly tightened. The former procedure has the advantage of reducing the amount of time during which the veins IVC, SVC are occluded. The latter procedure has the advantage of minimizing the amount of sizing required and permits use of a smaller size jacket 10, 10'. Snugly fitting a smaller size jacket 10, 10' reduces the amount of excess material which must be gathered. Either procedure is acceptable and is a matter of surgeon preference.

After the jacket 10, 10' is snugly tightened, the occlusion of the veins IVC, SVC may be relieved by deflating and removing the balloons 100, 102. In the absence of such occlusion, the heart H is inclined to expand to its original diastolic volume. However, such expansion is precluded by the restraining jacket 10, 10'. Therefore, the heart H retains its reduced diastolic size. Since the heart shape is maintained during the heart size reduction technique, heart function is not degraded in a manner which might otherwise accompany a mis-shaped reduced heart size. Such degradation of function may include, for example, valvular dysfunction or improper filling of the heart.

While the veins IVC, SVC are occluded, the areas of the body served by the veins IVC, SVC are deprived of blood flow as the flow blockage of un-oxygenated blood in the veins retards the flow of oxygenated blood to the area served by the veins. However, since the amount of time needed to place and secure the jacket 10, 10' is short, this ischemia period is acceptably short.

Balloons 100, 102 are shown in FIG. 6 occluding both the inferior and superior vena cava IVC, SVC. Such occlusion of both veins IVC, SVC is shown to illustrate a technique involving a high degree of blood restriction to achieve a high degree of heart size reduction. However, the present invention permits a regulated amount of occlusion to control the amount of heart size reduction to meet the particular needs of an individual patient. For example, only one of the veins IVC, SVC need be occluded. Further, either or both of the balloons 100, 102 can be only partially inflated to permit restricted blood flow through the veins IVC, SVC.

Using partial occlusion as described in the preceding paragraph, the amount of occlusion can be progressively increased. During such increase, the patient can be monitored to measure a responding reduction in heart size. When a desired amount of reduction is noted (e.g., a 30% reduction in diastolic volume), further occlusion is stopped and the heart size is retained at the desired level of reduction. The jacket 10, 10' can then be secured as previously described.

The amount of heart size reduction can be measured in any one of a number of ways. For example, heart size can be measured directly. Such direct measurements may include a measuring tape placed around the heart H or measuring images from echo imaging.

Figure 7:
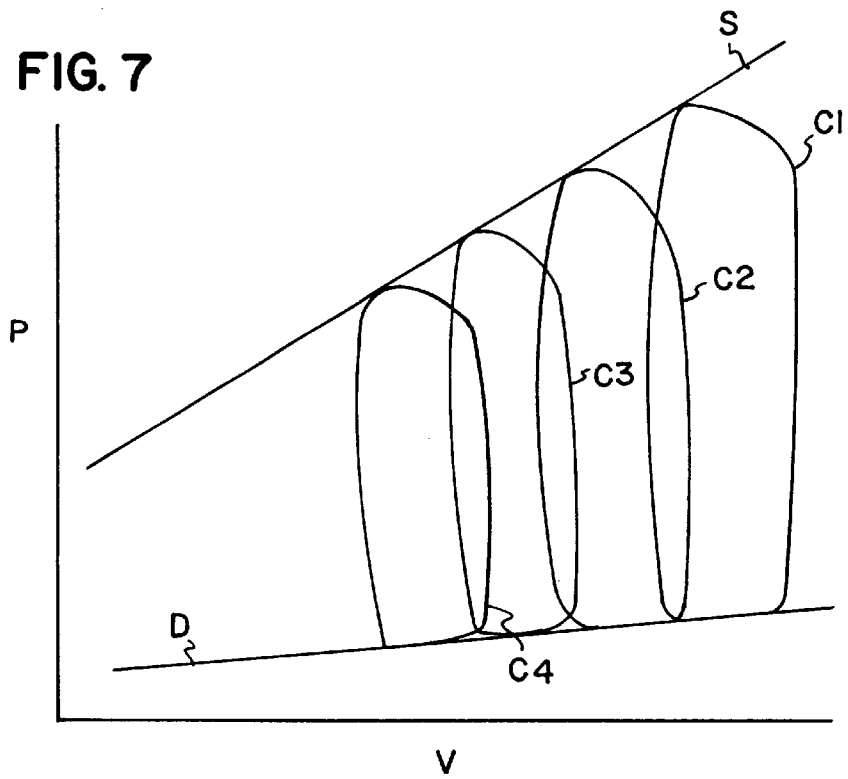
FIG. 7 is a graph showing heart pressure curves of a heart reducing in volume.

Heart size measurement may also be indirect. For example, heart pressure can be measured to provide an indication of heart volume reduction. This is illustrated in FIG. 7. In this figure, the abscissa represents heart volume V. The ordinate represents left ventricular pressure P. A first line S represents end systolic pressure and a second line D represents end diastolic pressure. Bounded curves C1, C2, C3 and C4 represent a pressure curve during successive heart beats of a heart which is reducing in volume. For example, curve C1 is a pressure curve during a heart beat of heart H prior to occlusion of the veins IVC, SVC. After full or partial occlusion, the heart size reduces and the pressure curve of a heart beat shifts to curve C2. During a subsequent beat, the curve shifts to curve C3 and eventually shifts to curve C4 which represents a steady-state curve for the reduced heart volume corresponding to the applied amount of occlusion. By monitoring the steady-state pressure curve C4, a physician can regulate the occlusion until achieving a desired steady-state pressure curve corresponding with a particular heart volume. To monitor pressure, a physician could use ventricular pressure (e.g., end systolic pressure) or aortic, arterial or pulse pressure as indirect measures of volume reduction.

From the foregoing detailed description, the invention has been described in a preferred embodiment. Modifications and equivalents of the disclosed concepts are intended to be included within the scope of the appended claims.

What is claimed is:

1. A method for treating cardiac disease of a heart having a longitudinal axis from an apex to a base and having an upper portion and a lower portion divided by an A-V groove, the heart including a valvular annulus adjacent the A-V groove and ventricular lower extremities adjacent the apex, the method comprising:

accessing the heart;

restricting a blood supply to the heart to reduce a size of the heart;

placing a constraining device on the heart and securing the constraining device to the heart with the constraining device having portions disposed on an exterior of the heart between the valvular annulus and the ventricular lower extremities to constrain circumferential expansion of the heart during diastole and permit unimpeded contraction of the heart during systole; and closing access to the heart while leaving the constraining device in place on the heart.

2. A method according to claim 1 further comprising restricting blood supply by at least partially occluding at least one vessel supplying blood to a right atrium of the heart.

3. A method according to claim 2 further comprising regulating occlusion of the vessel until a desired heart size attained.

4. A method according to claim 3 further comprising monitoring the heart size by monitoring heart pressure.

5. A method according to claim 1 further comprising restricting blood supply by at least partially restricting a diameter of vessels supplying blood to a right atrium of the heart.

6. A method according to claim 1 wherein the constraining device is placed on the heart before final reduction of the heart size and secured to the heart after final reduction of the heart size.

7. A method according to claim 1 further comprising placing and securing the constraining device after reduction of the heart size.

8. A method according to claim 1 comprising relieving the restricting following placement and securing of the constraining device.

* * * * *

UNITED STATES PATENT AND TRADEMARK OFFICE
CERTIFICATE OF CORRECTION

PATENT NO.    : 6,230,714 B1
DATED         : May 15, 2001
INVENTOR(S)   : Alferness et al.

It is certified that error appears in the above-identified patent and that said Letters Patent is hereby corrected as shown below:

Title page,
Item [54], please delete "METHODS" from the Title
Item [56], References Cited, U.S. PATENT DOCUMENTS, please insert the following at the end of the U.S. Patent list on the title page -- (List continued on next page.) --

Column 2,
Line 31, "In his procedure," should read -- In this procedure, --
Line 41, "stemotomy" should read -- sternotomy --

Column 10,
Line 46, "desired heart size attained" should read -- desired heart size is attained --

Signed and Sealed this

Tenth Day of June, 2003

JAMES E. ROGAN
*Director of the United States Patent and Trademark Office*